United States Patent
Falahatpisheh et al.

(10) Patent No.: US 10,345,132 B2
(45) Date of Patent: Jul. 9, 2019

(54) MULTI-PLANE METHOD FOR THREE-DIMENSIONAL PARTICLE IMAGE VELOCIMETRY

(71) Applicant: THE REGENTS OF THE UNIVERSITY OF CALIFORNIA, Oakland, CA (US)

(72) Inventors: Ahmad Falahatpisheh, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1402 days.

(21) Appl. No.: 13/886,680

(22) Filed: May 3, 2013

(65) Prior Publication Data
US 2014/0149055 A1    May 29, 2014

Related U.S. Application Data (60) Provisional application No. 61/642,786, filed on May 4, 2012, provisional application No. 61/777,288, filed on Mar. 12, 2013.

(51) Int. Cl.
| | | |
|---|---|---|
| *A61B 6/00* | (2006.01) | |
| *A61B 8/00* | (2006.01) | |
| *A61B 8/06* | (2006.01) | |
| *A61B 8/08* | (2006.01) | |
| *G01F 9/00* | (2006.01) | |
| *G01P 5/00* | (2006.01) | |

(52) U.S. Cl.
CPC .............. *G01F 9/001* (2013.01); *A61B 6/481* (2013.01); *A61B 6/504* (2013.01); *A61B 6/507* (2013.01); *A61B 8/06* (2013.01); *A61B 8/466* (2013.01); *A61B 8/483* (2013.01); *A61B 8/5223* (2013.01); *G01P 5/001* (2013.01); *A61B 6/484* (2013.01)

(58) Field of Classification Search
CPC ................ H04N 13/0203; G06V 1/303; G06F 17/5018; G06K 9/00; A61B 8/06; A61B 8/12; A61B 5/02028; A61B 5/02007; A61B 6/504; G01S 515/899; G01F 9/001; G01P 5/001
USPC ........... 606/130; 703/9, 10, 2; 600/454, 437; 382/132, 128
See application file for complete search history.

(56) References Cited

U.S. PATENT DOCUMENTS

| | | | |
|---|---|---|---|
| 6,511,426 B1* | 1/2003 | Hossack | ............... G01S 15/899 600/437 |
| 8,620,404 B2* | 12/2013 | Mistretta | ............... A61B 5/055 382/128 |

(Continued)

FOREIGN PATENT DOCUMENTS

| | | | | |
|---|---|---|---|---|
| WO | WO 2011/032210 A1 | | 3/2011 | |
| WO | WO 2011032210 A1 * | | 3/2011 | ............... A61B 5/08 |

(Continued)

*Primary Examiner* — Regis J Betsch
*Assistant Examiner* — Kaleria Knox
(74) *Attorney, Agent, or Firm* — Perkins Coie LLP (57) ABSTRACT

A multi-planar velocimetry approach to characterize 3D incompressible flows based on 2D perpendicular (or otherwise complementary) velocity fields is described. Two-dimensional velocity fields acquired on the planes are reconstructed into a 3D velocity field through interpolation and the imposition of a fluid incompressibility constraint.

25 Claims, 6 Drawing Sheets

(56) References Cited

U.S. PATENT DOCUMENTS

| | | | |
|---|---|---|---|
| 9,025,849 B2* | 5/2015 | Fouras | H04N 13/0203 |
| | | | 382/132 |
| 9,582,876 B2* | 2/2017 | Specht | A61B 5/02007 |
| 2005/0041842 A1* | 2/2005 | Frakes | G06K 9/3216 |
| | | | 382/128 |
| 2007/0021951 A1* | 1/2007 | Lee Seislink | G01V 1/303 |
| | | | 703/10 |
| 2007/0219766 A1* | 9/2007 | Duggleby | G06F 9/3879 |
| | | | 703/9 |
| 2008/0015440 A1 | 1/2008 | Shandas et al. | |
| 2008/0219535 A1* | 9/2008 | Mistretta | G06T 11/006 |
| | | | 382/131 |
| 2009/0248041 A1* | 10/2009 | Williams | A61B 8/12 |
| | | | 606/130 |
| 2010/0036253 A1* | 2/2010 | Vezina | A61B 5/02028 |
| | | | 600/453 |
| 2010/0189337 A1* | 7/2010 | Jandt | A61B 6/463 |
| | | | 382/132 |
| 2010/0241405 A1 | 9/2010 | De Guise et al. | |
| 2010/0286968 A1* | 11/2010 | Parashkevov | G06F 17/5018 |
| | | | 703/2 |
| 2011/0137623 A1 | 6/2011 | Indinger et al. | |
| 2012/0265075 A1* | 10/2012 | Pedrizzetti | A61B 8/06 |
| | | | 600/454 |
| 2013/0070062 A1* | 3/2013 | Fouras | A61B 6/486 |
| | | | 348/50 |

FOREIGN PATENT DOCUMENTS

| | |
|---|---|
| WO PCT/US/2013/039408 | 8/2013 |
| WO PCT/US2013/034908 | 11/2014 |

* cited by examiner

MULTI-PLANE METHOD FOR THREE-DIMENSIONAL PARTICLE IMAGE VELOCIMETRY

RELATED APPLICATIONS

This filing claims the benefit of U.S. Provisional Patent Application No. 61/642,786 filed May 4, 2012 and U.S. Provisional Patent Application No. 61/777,288, filed Mar. 12, 2013, each of which is incorporated by reference herein in its entirety for all purposes.

FIELD

The embodiments described herein relate to a real-time three-dimensional particle imaging velocimetry technique optionally applicable to echocardiography.

BACKGROUND

Echo Particle Image Velocimetry (Echo-PIV) is a non-invasive ultrasonic technique for finding the multi-component velocity vectors in opaque flows. It is based on particle image velocimetry (PIV), a common technique used for characterizing flow fields. Particles that may be used as flow tracers for such purposes include microbubbles filled with octafluoropropane encapsulated in either a lipid (DEFINITY®, Lantheus Medical Imaging, Inc.) or protein (Optison™, GE Healthcare) outer shell, both of which are FDA-approved for clinical use.

Echo-PIV has been found to be a promising approach, and the results obtained appear to be qualitatively meaningful. Blood flow pattern is the fingerprint of cardiac performance. Each heart disease has unique blood flow characteristics and any variation in the blood flow pattern may indicate a change in cardiac performance.

Currently, two-dimensional (2D) blood flow information—obtained by echocardiography—is widely used to quantify cardiac dysfunction. While very useful, this information does not provide sufficient accuracy for characterizing complex three-dimensional flows, such as the flow in the right heart or in hearts with congenital defects. However, the quantification of three-dimensional (3D) cardiac flow patterns has remained a challenging fluid dynamics problem and modern echocardiography-based velocimetry techniques cannot yet acquire data with sufficient spatial and temporal resolution to improve clinical diagnosis. With existing systems, this is believed to be mainly due to the limited frame rate of 3D echocardiographic acquisitions, a limitation imposed by the speed of the ultrasound wave in the tissue. The present application overcomes this and other limitations apparent to those with skill in the art.

SUMMARY

The embodiments described herein relate to an approach for multi-planar three-dimensional reconstruction of two dimensional Echo-PIV data. In this approach, an echocardiographic-based imaging modality can obtain three-dimensional blood velocity information from heart chambers and vasculature in or near real time. By "real time" what is meant is that the rate of image acquisition is fast enough to capture the pace of the cardiac flow.

The subject systems, devices, and methods provide a relatively low-cost technology that can be used in the clinical setting as a component of an echocardiography machine to provide further quantitative flow information to help immediate decision-making for cardiovascular patients. The technology allows real-time quantification of complex three-dimensional flow fields inside the heart in both time and space. Illustrative examples of such use are provided. With current ultrasound probe technology, simultaneous, multi-plane recording at a high frequency (e.g., 100 Hz and above) may be employed. Using this technology, simultaneous 2D velocity data in multiple planes are acquired and recombined a posteriori to reconstruct a 3D velocity field. By taking advantage of the physical constraint given by fluid incompressibility that relates different velocity components, a consistent 3D vector field can be generated.

More generally, a Multi-Planar Partical Image Velocimetry (MPPIV) approach to characterize 3D incompressible flows based on 2D perpendicular velocity fields is described. Here, two-dimensional, two-component velocity fields acquired on perpendicular planes (by ultrasound imaging with such advantages described above or by other imaging in association with models) are reconstructed into a 3D velocity field through interpolation and imposition of an incompressibility constraint on the fluid flow. This method can estimate the out-of-plane component of the velocity and results in a divergence-free 3D velocity field. In addition, the incompressibility condition improves the interpolated field in terms of streamline length, thereby providing more value as an analytical tool since the resulted flow is more physically meaningful.

One or multiple sets of perpendicular planes may be employed in such a methodology. Moreover, a different number of vertical vs. horizontal planes may be employed.

In testing the method, validation results revealed that increasing the number of perpendicular planes reduces error. In addition, for a divergence-free field with no noise, correction improvement was small. However, as the noise level became larger, resulting in a larger deviation of the divergence of the velocity from zero, the correction significantly improved the simply-interpolated velocity field.

Systems, devices, methods, features, and/or advantages of the subject matter described herein will be or will become apparent to one with skill in the art upon examination of the following figures and detailed description. It is intended that all such additional systems, devices, methods, features, and/or advantages be included within this description and be within the scope of the subject matter described herein, regardless of whether recited in this summary section. In no way should the features of the example embodiments in this or any other section be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Variations other than those shown in the figures are contemplated as described in a broader sense in the above summary section, as generically claimed, or otherwise.

DETAILED DESCRIPTION

Various example embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act, or step to the objective(s), spirit, or scope of the present inventive subject matter. All such modifications are intended to be within the scope of the claims made herein.

Figure 1:
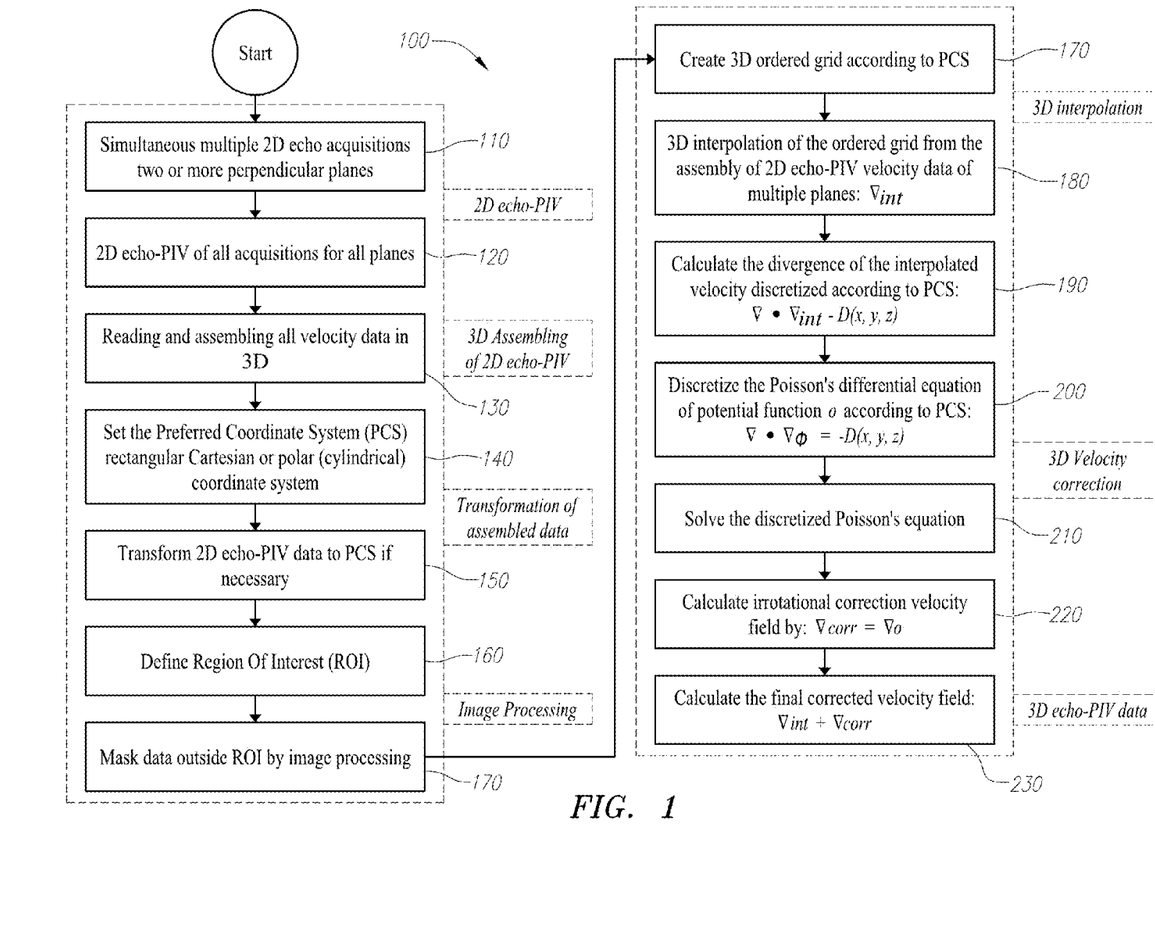
FIG. 1 is a flowchart detailing a method embodiment and associated software design.

FIG. 1 details one embodiment of the methodology 100. In this embodiment, simultaneous multiple two dimensional ultrasound acquisitions are performed in real time for three-dimensional reconstruction of the flow field. These acquisitions are captured using a suitable scanner or probe at 110. At 120, two-dimensional Echo-PIV is used to capture in-plane velocity components in a slice of the domain for each of the planes. Together, such activity may be regarded as performing 2D echo-PIV.

In other embodiments, non-simultaneous imaging may be employed as in some of the examples below that are reliant on flow periodicity to assemble suitable image plane data. Likewise, while ultrasound-based velocimetry techniques are preferred or necessary in vivo (e.g., for cardiac blood flow interrogation), optical approaches may be applied in vitro as discussed.

In any case, two or more perpendicular planes of captured data are employed for three-dimensional reconstruction of the flow field (i.e., for MPPIV). For each plane, the velocity vectors are calculated based on optical flow techniques, which are in turn based on finding the displacement vector that maximizes the correlation between the corresponding regions of interest (ROIs) in two consecutive frames. The results measure the displacement and velocity vectors of the acoustically (or otherwise) illuminated micro-bubbles in all ROIs within each image. The three-dimensional reconstruction of the flow will be performed through the careful assembling of all of the velocity information. To achieve this goal, a process has been developed to read, sort, and assemble all the velocity data of two (or more) perpendicular slices obtained from echo images with contrast.

Reading and assembling all of the obtained velocity data (e.g., 3D assembly of the 2D PIV) occurs at 130. Optionally, the echo-PIV (or other PIV) data are transformed from polar coordinates to rectangular Cartesian coordinates by using transformations: x=r cos θ and y=r sin θ where x and y are the Cartesian coordinates, r is the radius, and θ is the phase of each point in two dimensional echo-PIV plane. It is also possible to keep the polar coordinate system, and discretize the divergence equation (1), below, in the cylindrical coordinate system. In any case, a preferred coordinate system is set at 140 and any subsequent coordinate transformation occurs at 150. Together, such activity may be regarded as transformation of the assembled data.

Next, image processing is employed. A Region of Interest (ROI) is defined at 160. At 170, a predefined mask filters out the stationary parts of the images and detects the moving boundary of the ROI via image processing techniques well known in the art.

In the example where the preferred coordinate system (PCS) is Cartesian, an ordered three-dimensional Cartesian mesh will be generated with a velocity field that may be obtained by Kriging interpolation of the three-dimensional velocity vector field. Kriging is a group of geostatistical techniques that can be used to interpolate the value of a random field at an unobserved location from observations of its value at nearby locations. This 3D interpolation step first involves creating an ordered grid according to the PCS at 170. At 180, interpolation (optionally as described above) then proceeds from the assembly of 2D echo-PIV velocity data of the multiple planes.

Since the interpolated velocity field does not necessarily satisfy the incompressibility condition of the flow in three-dimensional space, the field is modified accordingly. In this regard, an irrotational velocity field having a divergence that cancels out the divergence of the interpolated velocity field will be added to it. 3D velocity correction performed in this manner creates a divergence-free velocity field that satisfies the incompressibility condition of the flow.

Following the theory developed for the fractional step method in computational fluid dynamics, the interpolated velocity field is projected into a divergence-free subspace. This projection is carried out by an appropriate pressure distribution to correct the velocity field. In fact, it is the gradient of the pressure distribution in the Navier-Stokes equations that significantly affects the divergence of the velocity field.

At 190, the divergence of the interpolated velocity field, D, is computed as:

$$\nabla \cdot V_{int} = \frac{\partial u_{int}}{\partial x} + \frac{\partial v_{int}}{\partial y} + \frac{\partial w_{int}}{\partial z} = D(x, y, z) \quad (1)$$

Since the velocity field has been interpolated in a Cartesian grid, where $x=x_1, x_2, x_i, \ldots, x_{NX}$, $y=y_1, y_2, y_j, \ldots, y_{NY}$ and $z=z_1, z_2, z_k, \ldots, z_{NZ}$ it follows that:

$$\frac{u_{int_{i+1,j,k}} - u_{int_{i-1,j,k}}}{x_{i+1} - x_{i-1}} + \frac{v_{int_{i+1,j,k}} - v_{int_{i-1,j,k}}}{y_{j+1} - y_{j-1}} + \frac{w_{int_{i+1,j,k}} - w_{int_{i-1,j,k}}}{z_{k+1} - z_{k-1}} = \qquad (2)$$
$$-D(x_i, y_j, z_k)$$

where the derivatives are calculated with $2^{nd}$ order accuracy. And u, v, w are the components of the velocity in a rectangular Cartesian coordinate system.

Having D calculated, at 200, a potential $\phi$ is sought through a Poisson differential equation:

$$\nabla \cdot (\nabla \phi) = -D \qquad (3)$$

which is discretized with 2nd order accuracy as:

$$\frac{\phi_{i+1,j,k} - 2\phi_{i,j,k} + \phi_{i-1,j,k}}{(x_{i+1} - x_{i-1})^2} + \frac{\phi_{i,j+1,k} - 2\phi_{i,j,k} + \phi_{i,j-1,k}}{(y_{j+1} - y_{j-1})^2} + \qquad (4)$$
$$\frac{\phi_{i,j,k+1} - 2\phi_{i,j,k} + \phi_{i,j,k-1}}{(z_{k+1} - z_{k-1})^2} = -D(x_i, y_i, z_k)$$

This results in a linear system through which the potential $\phi_{i,j,k}$ can be solved at 210 by various methods such as a biconjugate gradient stabilized method or fast Fourier transform.

Therefore, the irrotational correction velocity field will be the gradient of the potential:

$$V = ui + vj + wk = \nabla \phi \qquad (5)$$

where the components of the velocity can be calculated at 220 with 2nd order accuracy by:

$$u_{i,j,k} = \frac{\phi_{i+1,j,k} - \phi_{i-1,j,k}}{x_{i+1} - x_{i-1}}, \; v_{i,j,k} = \frac{\phi_{i,j+1,k} - \phi_{i,j-1,k}}{y_{j+1} - y_{j-1}} \text{ and} \qquad (6)$$
$$w_{i,j,k} = \frac{\phi_{i,j,k+1} - \phi_{i,j,k-1}}{z_{k+1} - z_{k-1}}$$

The final corrected velocity field, $V_{int} + V$, (i.e., the 3D echo-PIV data) at 230 therefore satisfies flow incompressibility and continuity conditions.

Example 1

Figure 2:
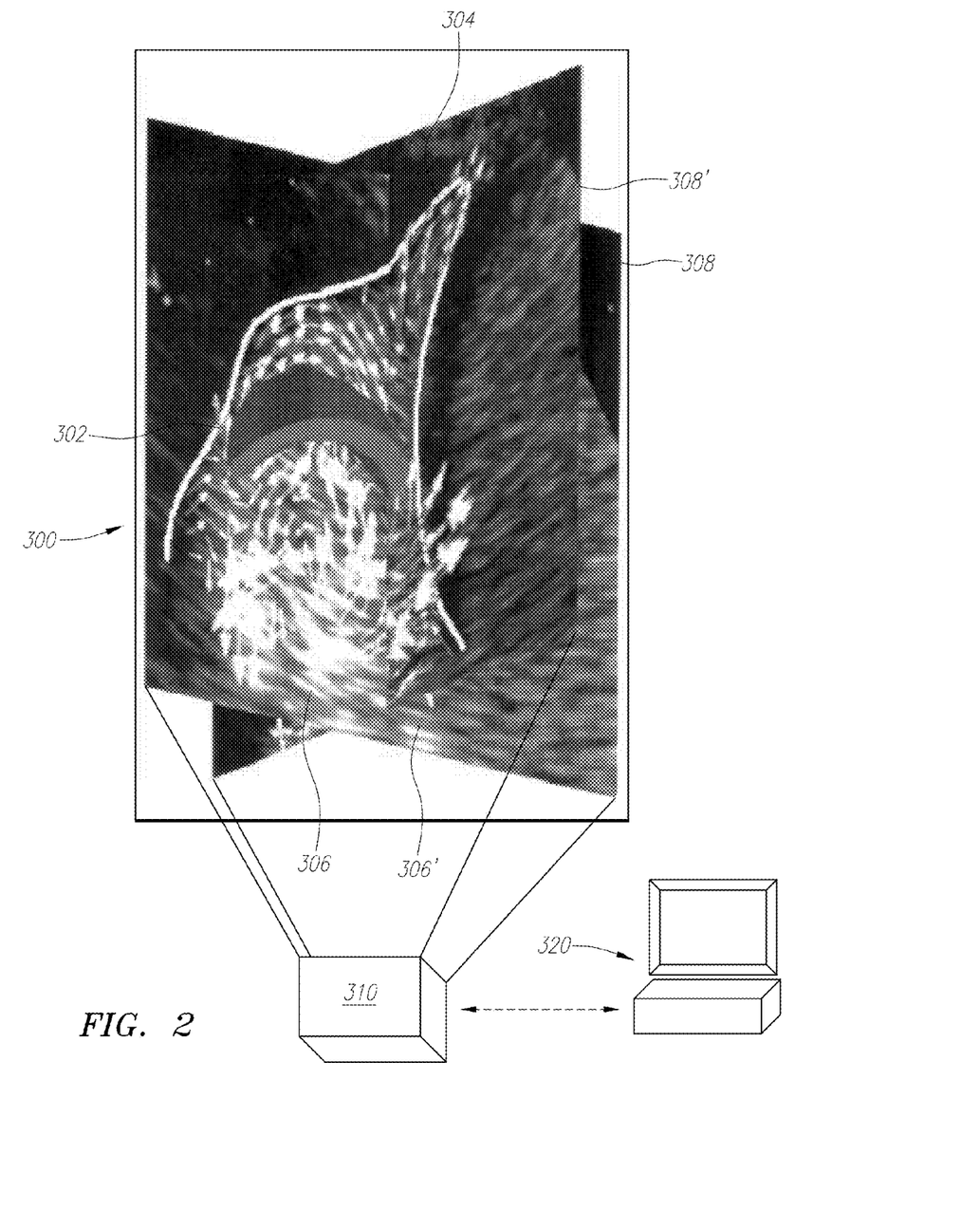
FIG. 2 illustrates an example of 3D Echo-PIV results accomplished with the subject methods.

3D-echo PIV was performed in connection with a living human subject in accordance with such methodology. FIG. 2 illustrates a calculated flow vortex 300 formed from a trans-tricuspid jet during right ventricle (RV) diastole together with a multi-plane ultrasound imaging probe 310 and a suitable computer system 320 for receiving and processing probe image data, which systems may be connected for data transmission by wired or wireless means as indicated by the arrows. Vortex 300 is represented in 3D as a u-shaped curve by iso-surfaces of $\lambda_2$ 302 calculated from the velocity vector field (not shown) obtained from the subject 3D echo-PIV methodology. The Region of Interest (ROI) 304 is indicated by a white line defining the RV boundaries. The vectors shown are inplane velocities 306, 306' acquired by 2D echo-PIV in two complementary perpendicular planes 308, 308' intersecting the RV axis.

Examples 2A and 2B

The behavior of the reconstruction method detailed above was also systematically verified. Two examples with 3D divergence-free interpolated flow fields were compared to benchmark situations with known flow features: (1) a Hill Spherical Vortex (HSV); and (2) a 3D DNS flow field behind a slender orifice. The benchmark velocity fields with known solutions are hereinafter referred to as "true" solutions.

Example flow fields were sampled in two perpendicular stacks of planes (xy- and yz-stacks). Different image slices (otherwise, optionally, referred to as image planes) of the stacks were acquired using a single high-speed camera (Y3, IDTVision, Inc.), which can be replaced by an ultrasound matrix probe. A single camera was used for acquiring different slices of the stack in sequence by taking advantage of the periodicity of the flow. With a multi-slice acquisition source (e.g., a matrix array ultrasound transducer for multi-planar Echo-PIV), 2D velocity fields can be acquired simultaneously on each slice of the stacks.

For each slice or image plane, the out-of-plane component of velocity was disregarded. The sampled data was generated for four different stacks with different numbers of samples. In all the stacks, each slice contained 32×32 samples, which were uniformly distributed. Slices in each stack were either 4, 8, 16, or 32 in number. In each stack, the distance between the slices was the same, which created a uniform stack. Furthermore, to mimic the uncertainty associated with experimentally-acquired velocity measurements, different levels of noise were introduced to the sampled data by starting from a field with no noise, then adding 15% and 30% Gaussian noise levels relative to the 3D field velocity scale. Therefore, for each benchmark flow field, a total of twelve sampled datasets were generated.

In all of these tests cases, 3D divergence-free interpolated velocity fields were obtained with a resolution of $64^3$ and compared with the true solution at the same points. The Root Mean Square (RMS) error, reported here as a function of the number of slices in the stack, statistically represents the difference between either the simply-interpolated or the divergence-free interpolated velocity field and the true solution $$Err_{RMS_i} = \frac{\sqrt{\frac{1}{n}\Sigma[(u_T - u_i)^2 + (v_T - v_i)^2 + (w_T - w_i)^2]}}{\text{Velocity Scale}} \qquad (7)$$

where $n = 64^3$ is the resolution of the three-dimensional domain, subscript T stands for true velocity field, and subscript i can be either the simply-interpolated or divergence-free interpolated velocity field.

2A: HSV Benchmark

The Hill Spherical Vortex (HSV) is a convenient benchmark for the purpose of flow validation. This vortex is an extreme member of the Norbury family of vortex rings that is used as a model in applications such as the motion of bubbles and droplets at high Reynolds number. The vorticity inside the HSV varies linearly with the distance from the axis of symmetry. The external flow is irrotational around a sphere, whereas the internal flow attributes to an axisymmetric vorticity distribution. The spherical symmetry of the HSV vector field challenges the subject methodology when computed in a Cartesian grid.

Figure 3A:
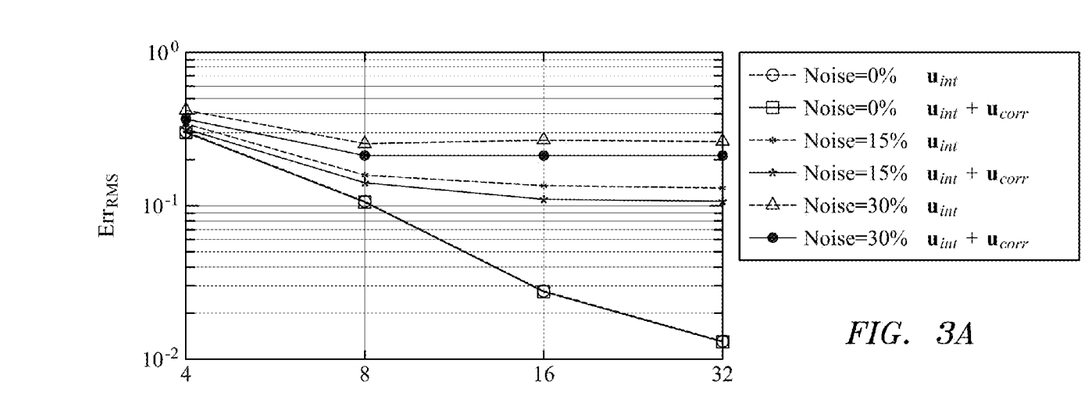
FIGS. 3A and 3B chart RMS error for additional examples considering Hill's Spherical Vortex (HSV) and Domenichini's DNS velocity field models, respectively.

FIG. 3A shows the RMS error calculated for the simply-interpolated and divergence-free interpolated velocity fields generated according to the subject methodology in comparison with a HSV having a unit radius and velocity scale in a cube of size 1.5×1.5×1.5. Per above, 0%, 15%, 30% Gaussian noise was applied to 4, 8, 16, and 32 xy- and yz-slices captured at 32×32 resolution. In all the cases, the divergence-free interpolated velocity field showed an improvement with respect to the simply-interpolated field. When no noise was introduced in the sampled data, the RMS error was not significantly reduced by applying the incompressibility constraint, mainly because the sampled velocity field was already divergence-free, thus providing an indirect validation of the interpolation procedure. However, as the level of noise increased, the divergence correction adjusted the interpolated flow field more significantly towards reducing the difference in RMS error. In other words, the greater the level of uncertainty in the velocimetry data, the greater the benefit of ensuring the incompressibility constraint.

2B: 3D DNS Benchmark

The 3D velocity field behind a slender orifice as investigated by Domenichini (i.e., a 3D DNS flow field) was used as a second benchmark. In Domenichini's study, the three-dimensional vortex formation due to the impulsively started flow through slender openings was numerically simulated.

Figure 3B:
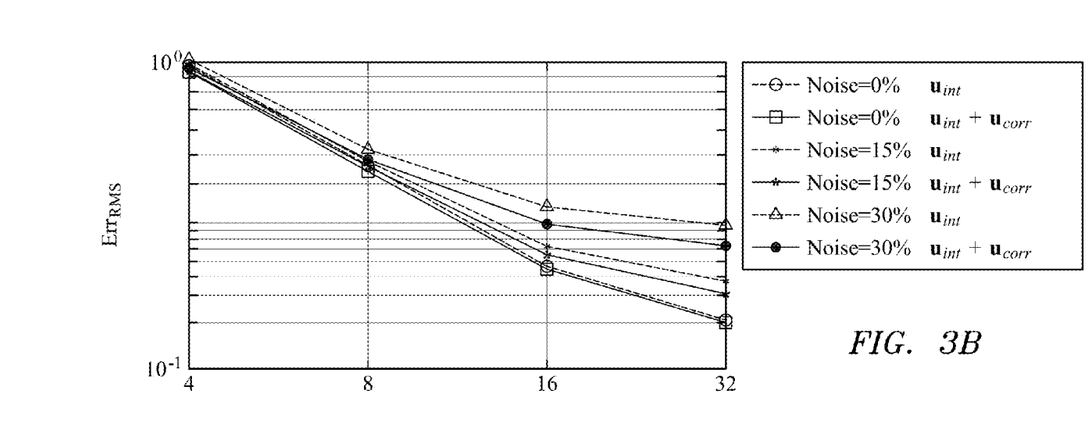

FIG. 3B shows the RMS error calculated for the simply-interpolated and divergence-free interpolated velocity fields of sample data taken versus the number of slices with Domenichini's DNS velocity field taken as the true solution. Again, 0%, 15%, 30% Gaussian noise was applied to 4, 8, 16, and 32 xy- and yz-slices captured at 32×32 resolution. In agreement with the previous findings for the HSV, that data demonstrates that imposing the incompressibility constraint improves the accuracy of the flow field, and this improvement is more prominent with increasing levels of noise-to-signal ratio.

Example 3

In this example, the MPPIV method is tested in an actual experimental setting. This test case provides preliminary experimental observations of the flow inside a model of the right ventricle.

Figure 4:
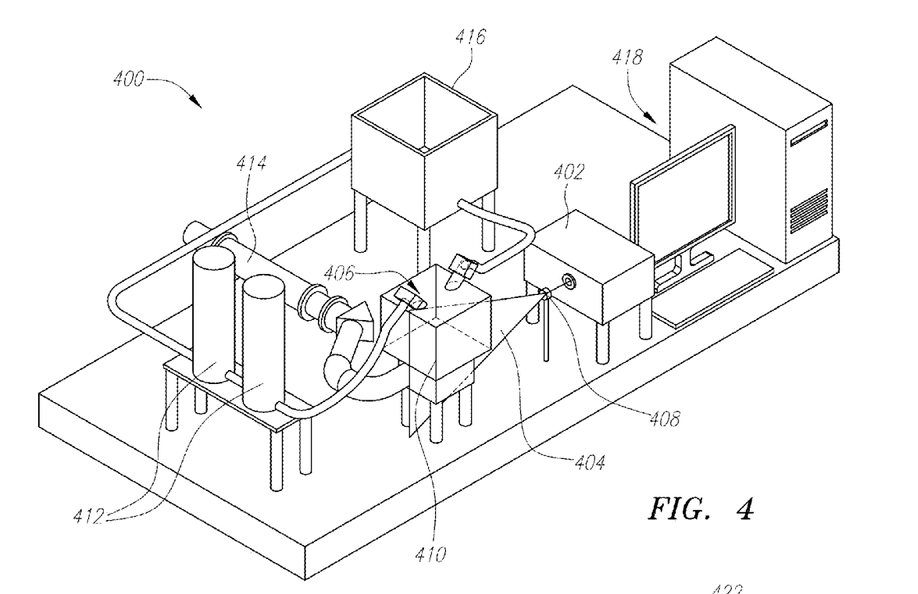
FIG. 4 is a schematic illustrating a pulsatile heart-flow simulator for MPPIV experimentation and flow modeling setup for another example.
Figure 5:
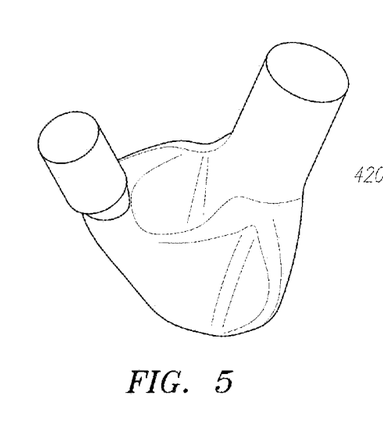
FIG. 5 illustrates the shape of a Right Ventricle (RV) cast for the manufacture of a silicone rubber model for the flow simulator of FIG. 4.

FIG. 4 is a schematic illustrating a pulsatile heart-flow simulator 400 employed for such purposes. The system includes an Nd:YLF green pump laser 402, a laser light sheet 404 for illumination of micro-fluorescent particles (not shown) inside a model 406 of the right ventricle (RV), a cylindrical lens 408 for converting laser beam light to the laser sheet, a box 410 filled with water containing RV model 406, resistance chambers 412 for adjusting the systemic venous and right atrial pressures in the RV model, a positive displacement pump 414 for creating pulsatile flow in the RV model; an open-to-atmosphere lung reservoir 416; and a computer system 418 for acquisition and/or processing. The geometry of the RV model 406 in the pumping phase is shown in FIG. 5. The geometry was generated using 3D echocardiography of a human subject.

Using simulator 400, the subject method was applied to quantify the flow in the RV model. Although flow inside the left heart has been extensively investigated, both in vitro and in vivo, very little quantitative information is available on flow patterns inside the right heart. The particular reasons for this include: (1) the non-symmetric, crescent shape of the RV, which is wrapped around the left ventricle (LV) and limits 2D echocardiographic flow evaluations, and (2) the highly time-dependent nature of RV flow.

Figure 6:
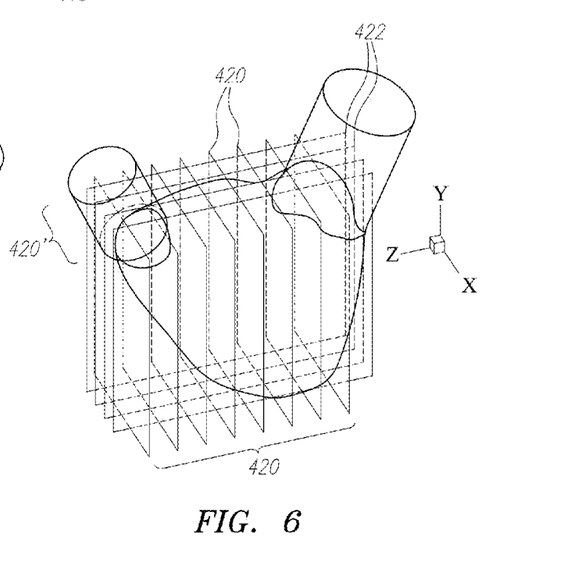
FIG. 6 illustrates a schematic of the two perpendicular stacks used for 3D reconstruction of the RV velocity field for the model of FIG. 5.

FIG. 6 illustrates the capture of planar velocity fields from two perpendicular stacks 420, 420' including a total of 12 slices 422, 422' covering the entire RV chamber. In the experiment, these were captured at 1000 frame per second (fps) with a high-speed camera per above. Taking advantage of the periodicity of the flow and the fine temporal resolution of the camera, the velocity field in each slice was acquired separately and in sequence with a single camera. Stack 420 included 8 xy-slices 422 and stack 420' included 4 yz-slices 422' to cover the model.

Figure 7:
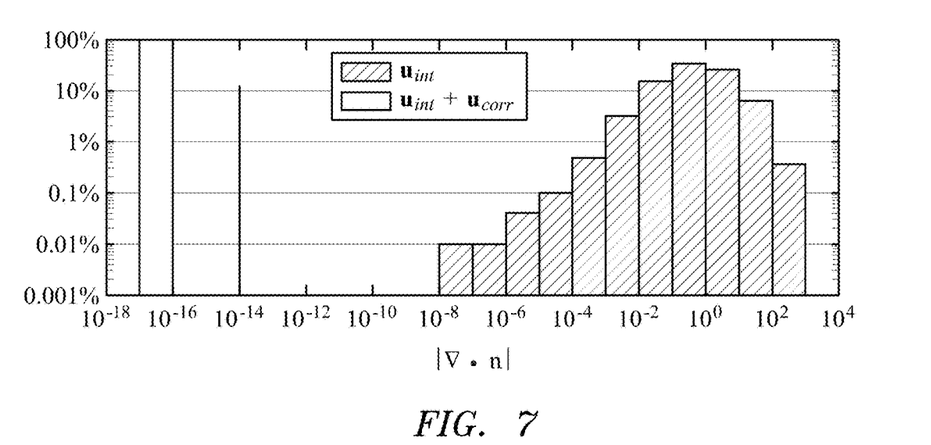
FIG. 7 charts the absolute value of divergence of the interpolated velocity field normalized by the total number of the grids inside the RV model.

FIG. 7 shows a histogram of the divergence of the simply-interpolated velocity. Out of 643 grid points, 220, 272 points inside the RV model were considered for analysis. Bins without any bars represent zero counts. The line on $10^{-14}$ belongs to the case of the simply-interpolated velocity field and represents all the grids whose absolute velocity divergence is less than 10-14. For the divergence-free field, all of the grids exhibited an absolute divergence value less than 10-16 as shown by the red bar. Thus, the majority of the flow field initially exhibited a non-physical divergence. Therefore, the incompressibility correction (numerically $|\nabla \cdot V| < 10^{-16}$) represents an important step in the creation of a 3D velocity vector field.

This conclusion can also be recognized by studying the flow streamlines that were found to be mostly continuous in the divergence-free interpolated field, whereas in the simply-interpolated field they were shorter and disconnected. To quantitatively verify this matter, 4,913 streamlines were generated inside the RV model. The streamline lengths were calculated and normalized by the maximum streamline length in the divergence-free velocity field.

Figure 8:
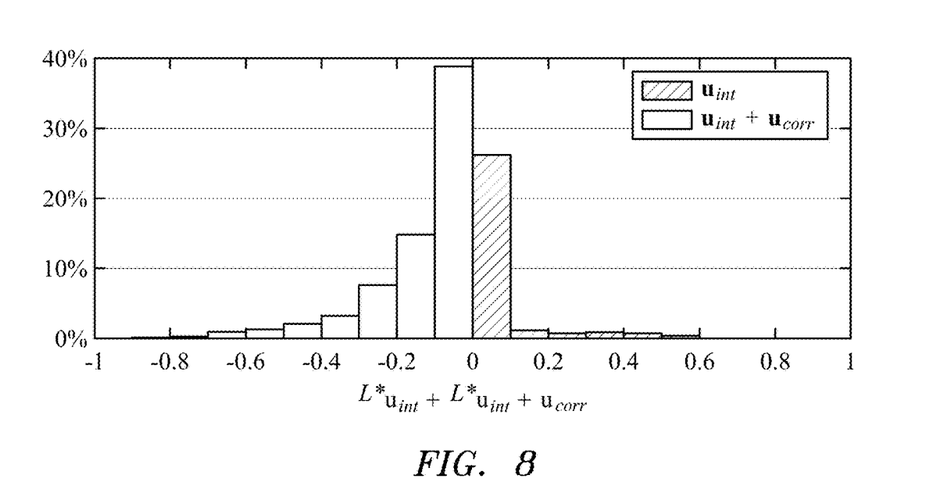
FIG. 8 charts the difference in normalized streamline length inside the RV model between the simply interpolated and divergence-free interpolated velocity fields.

FIG. 8 shows the histogram of the length difference between streamlines, originating from the same points, in the divergence-free interpolated and the simply-interpolated velocity fields. It is evident that the length of streamlines increased after imposing the incompressibility constraint in a majority of the cases.

Figure 9A:
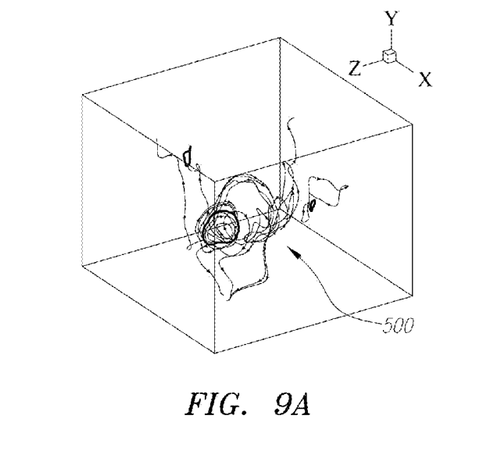
FIGS. 9A and 9B illustrates streamlines of the RV model with FIG. 9A showing some streamlines in the simply-interpolated velocity field and FIG. 9B showing the streamlines originating at the same points for the divergence-free interpolated velocity field.
Figure 9B:
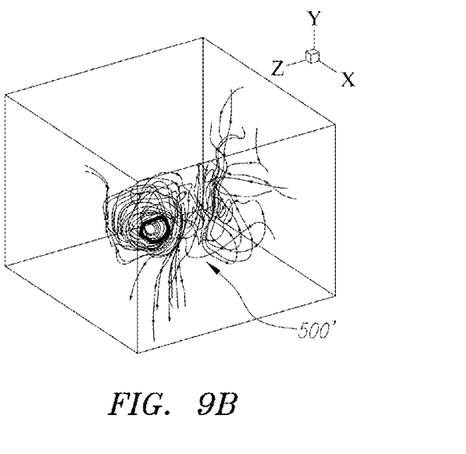

FIGS. 9A and 9B show several sample streamlines to support the physical interpretation of this result. Specifically, FIG. 9A shows some streamlines 500 in the simply interpolated velocity field. FIG. 9B illustrates streamlines 500' originating at the same points for the divergence-free interpolated velocity field.

Figure 10A:
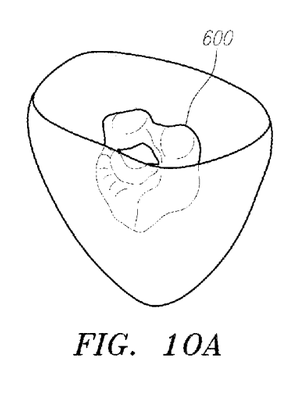
FIGS. 10A-10C illustrate selected iso-surfaces of the flow inside the RV model.
Figure 10B:
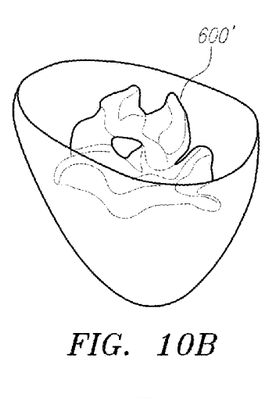
Figure 10C:
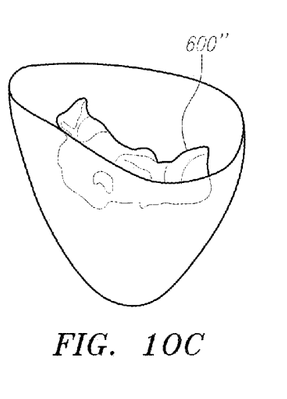
Figure 11:
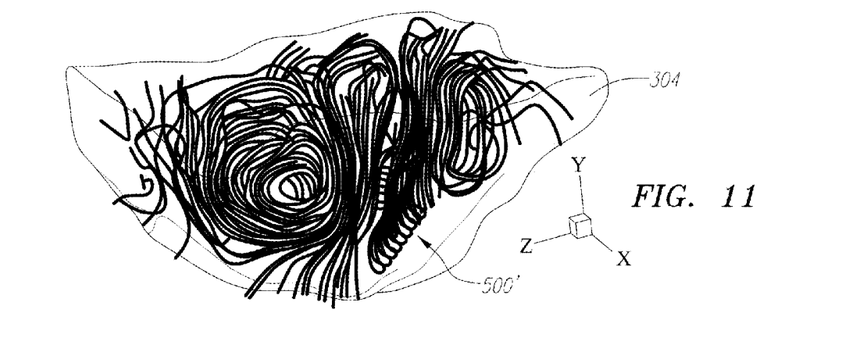
FIG. 11 illustrates colored-coded velocity streamlines of the 3D divergence-free interpolated velocity field inside the RV model during an early filling phase of the model.

So-considered, FIGS. 10A-10C illustrate the iso-surfaces 600, 600', 600" of $\lambda_2$ for t=22, 136, and 699 ms for the model. During the first 650 ms out of a 1000 ms duration for the cardiac cycle, the inlet valve (i.e. the model's tricuspid valve) on the right side of the FIGS. 6A and 6B was open and the RV model was in the filling phase. With the flow reconstructed using MPPIV, a vortex ring was formed shortly after the inlet valve opened as shown in FIG. 11A. One side of the ring then interacted with the nearby wall and gave rise to an enhanced local dissipation that altered the vortex structure as shown in FIG. 11B. At the end of the filling phase, the inlet valve closed and the outlet valve (i.e., the pulmonary valve) opened for the next 350 ms of the cycle, pumping the fluid out of the RV model. In this phase, the vortex structure took the shape of a streamline filament elongating toward the exit as shown in FIG. 11C, which corresponds to a helical motion along the converging outflow tract.

Variations

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments of the invention.

The various illustrative logical blocks, modules, and circuits described in connection with the embodiments disclosed herein, may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, display port, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other. Moreover, the operations may be carried out in any order of events which is logically possible, as well as any recited order of events.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. No limitations from the specification are intended to be read into any claims, unless those limitations are expressly included in the claims. Reference to a singular item includes the possibility that there are a plurality of the same items present. More specifically, as used herein and in the appended claims, the singular forms "a," "an," "said," and "the" include plural referents unless specifically stated otherwise. In other words, use of the singular forms allow for "at least one" of the subject item in the description above as well as the claims below. It is further noted that the claims may exclude any optional element and may explicitly limit each element to a "single" instance or "only one" such instance of that element. As such, this paragraph is intended to serve as antecedent basis for the use of such exclusive terminology as "solely," "only," "a single" and the like in connection with the recitation of claim elements, or the use of a negative limitation.

Without the use of such exclusive terminology, the terms "comprising," "including," and "having" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein. Also, it is contemplated that any optional feature of the described variations may be set forth and claimed independently, or in combination with any one or more of the features described herein.

The breadth of the different embodiments or aspects described herein is not to be limited to the examples provided and/or the subject specification, but rather only by the scope of the issued claim language.

The invention claimed is:

1. A method for improving detection of blood flow variations, the method comprising:
   acquiring cardiac blood velocimetry data in multiple 2-D planes having different angles with respect to each other, the velocimetry data acquired based on data obtained one or more probes or scanners;
   determining only in-plane velocity components for each of the multiple 2-D planes having different angles with respect to each other using the acquired velocimetry data;
   determining, using Kriging interpolation, a three-dimensional interpolated-velocity field with only the determined in-plane velocity components of each plane while discarding an out-of-plane velocity component of each plane;
   generating an improved cardiac blood flow visualization model using the three-dimensional interpolated velocity field; and
   displaying a physical interpretation of the improved cardiac blood flow visualization model to allow the detection of blood flow variations, wherein a system for acquiring cardiac blood velocimetry data includes an optical camera.

2. The method of claim 1, wherein the velocimetry data is acquired through processing image data selected from image-velocimetry techniques, magnetic resonance imaging, ultrasound-based velocimetry and computed tomography methods.

3. A method for improving detection of blood flow variations, the method comprising:
   acquiring cardiac blood velocimetry data in multiple 2-D planes having different angles with respect to each other, the velocimetry data acquired based on data obtained one or more probes or scanners;
   determining only in-plane velocity components for each of the multiple 2-D planes having different angles with respect to each other using the acquired velocimetry data;
   determining, using Kriging interpolation, a three-dimensional interpolated-velocity field with only the determined in-plane velocity components of each plane while discarding an out-of-plane velocity component of each plane;
   generating an improved cardiac blood flow visualization model using the three-dimensional interpolated velocity field; and
   displaying a physical interpretation of the improved cardiac blood flow visualization model to allow the detection of blood flow variations, wherein the velocimetry data is obtained with a system for observing and imaging a domain of flow tracers in the multiple planes, the flow tracers being acoustically illuminated micro-bubbles.

4. The method of claim 1, further comprising outputting the interpolated velocity field.

5. The method of claim 4, further comprising adding, to the interpolated velocity field, an irrotational velocity field with a divergence to cancel out a divergence of the interpolated velocity field to create a divergence-free velocity field that satisfies an incompressibility condition of fluid flow.

6. The method of claim 5, wherein the interpolated velocity field does not satisfy the incompressibility condition of fluid flow in three dimensions.

7. The method of claim 1, wherein the multiple 2-D planes include a number of planes having different, arbitrary angles with respect to each other and with respect to a chosen coordinate system that is selected from a group consisting of a Cartesian system, a Cylindrical system and a Spherical coordinate system.

8. The method in claim 1, where in the multiple 2-D planes are perpendicular with respect to each other.

9. The method of claim 7, wherein the multiple 2-D planes include a number of parallel planes with respect to the chosen coordinate system.

10. The method of claim 1, wherein the velocimetry data is transformed to rectangular Cartesian coordinates.

11. The method of claim 1, further comprising:
   filtering out stationary parts of the images using a predefined mask.

12. The method of claim 1, further comprising:
   detecting a moving boundary of a region of interest.

13. The method of claim 1, wherein the Kriging interpolation comprises using a geostatistical technique to interpolate values of a random field at an unobserved location.

14. The method of claim 1, further comprising projecting the interpolated velocity field into a divergence-free subspace.

15. The method of claim 1, wherein the system includes an ultrasound transducer.

16. The method of claim 1, wherein the velocimetry data is obtained with a system for observing and imaging a domain of flow tracers in multiple planes, the flow tracers being acoustically illuminated micro-bubbles.

17. A computer readable medium having stored thereon instructions, which when executed cause one or more processors to:
   receive input signals corresponding to cardiac blood velocimetry data in multiple planes having arbitrary angles with respect to each other, the input signals having been obtained based on data acquired by one or more probes or scanners in a system for observing and imaging a domain of flow tracers in the multiple planes, the flow tracers being acoustically illuminated micro-bubbles;
   determine in-plane velocity components for each plane;
   determine, using Kriging interpolation, an interpolated three-dimensional velocity field, using only the in-plane velocity components while disregarding all out-of-plane velocity components;

generate an improved cardiac blood flow visualization model using the interpolated three-dimensional velocity field; and displaying a physical interpretation of the improved cardiac blood flow visualization model to allow the detection of blood flow variations.

18. The computer readable medium of claim 17, wherein the instructions when executed further cause the one or more processors, to the interpolated velocity field, an irrotational velocity field with a divergence to cancel out a divergence of the interpolated velocity field to create a divergence-free velocity field that satisfies an incompressibility condition of fluid flow.

19. A system for improving detection of blood flow variations, the system comprising:

a probe to acquire cardiac blood velocimetry data in multiple 2-D planes having different angles with respect to each other; and a processor and a memory including processor executable code, the processor executable code when executed by the processor configures the processor to:

determine only in-plane velocity components for each of the multiple 2-D planes having different angles with respect to each other using the acquired velocimetry data, determine, using Kriging interpolation, a three-dimensional interpolated velocity field with only the determined in-plane velocity components of each plane while disregarding an out-of-plane velocity component of each plane, and generate an improved cardiac flow visualization model using the three-dimensional interpolated velocity field; and display of a physical interpretation of the improved cardiac blood flow visualization model to allow the detection of blood flow variations, wherein the system includes an optical camera.

20. The system of claim 19, wherein the processor is further adapted to add, to the interpolated velocity field, an irrotational velocity field with a divergence to cancel out a divergence of the interpolated velocity field to create a divergence-free velocity field that satisfies an incompressibility condition of fluid flow.

21. The computer readable medium of claim 17, wherein the instructions when executed further cause the one or more processors to detect a moving boundary of a region of interest.

22. The computer readable medium of claim 17, wherein the multiple 2-D planes include a number of planes having different, arbitrary angles with respect to each other and with respect to a particular coordinate system.

23. A system for improving detection of blood flow variations, the system comprising:

a probe to acquire cardiac blood velocimetry data in multiple 2-D planes having different angles with respect to each other and including a system for observing and imaging a domain of flow tracers in the multiple planes, the flow tracers being acoustically illuminated micro-bubbles; and a processor and a memory including processor executable code, the processor executable code when executed by the processor configures the processor to:

determine only in-plane velocity components for each of the multiple 2-D planes having different angles with respect to each other using the acquired velocimetry data, determine, using Kriging interpolation, a three-dimensional interpolated velocity field with only the determined in-plane velocity components of each plane while disregarding an out-of-plane velocity component of each plane, and generate an improved cardiac flow visualization model using the three-dimensional interpolated velocity field; and display of a physical interpretation of the improved cardiac blood flow visualization model to allow the detection of blood flow variations, wherein the system includes an optical camera.

24. The system of claim 23, wherein the processor executable code when executed by the processor further configures the processor to detect a moving boundary of a region of interest.

25. The system of claim 23, wherein the multiple 2-D planes include a number of planes having different, arbitrary angles with respect to each other and with respect to a particular coordinate system.

* * * * *